(12) United States Patent
Chu

(10) Patent No.: US 9,044,220 B2
(45) Date of Patent: Jun. 2, 2015

(54) DELIVERING PELVIC FLOOR REPAIR IMPLANTS

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 714 days.

(21) Appl. No.: 13/083,076

(22) Filed: Apr. 8, 2011

(65) Prior Publication Data

US 2011/0270026 A1 Nov. 3, 2011

Related U.S. Application Data

(60) Provisional application No. 61/330,227, filed on Apr. 30, 2010.

(51) Int. Cl.
| | |
|---|---|
| *A61B 17/04* | (2006.01) |
| *A61B 17/062* | (2006.01) |
| *A61B 17/29* | (2006.01) |
| *A61B 17/00* | (2006.01) |
| *A61B 17/06* | (2006.01) |

(52) U.S. Cl.
CPC ......... *A61B 17/0469* (2013.01); *A61B 17/0482* (2013.01); *A61B 17/0625* (2013.01); *A61B 17/2909* (2013.01); *A61B 2017/00278* (2013.01); *A61B 2017/00805* (2013.01); *A61B 2017/00867* (2013.01); *A61B 2017/00946* (2013.01); *A61B 2017/047* (2013.01); *A61B 2017/06028* (2013.01); *A61B 2017/2905* (2013.01); *A61B 2017/2911* (2013.01); *A61B 2017/2929* (2013.01)

(58) Field of Classification Search
CPC .......... A61B 17/0469; A61B 17/0625; A61B 17/04; A61B 17/0482; A61B 2017/00663
USPC ................. 600/29–31, 37; 606/139, 144–146
See application file for complete search history.

(56) References Cited

U.S. PATENT DOCUMENTS

| | | | |
|---|---|---|---|
| 6,048,351 A | 4/2000 | Gordon et al. | |
| 6,346,111 B1 | 2/2002 | Gordon et al. | |
| 7,041,111 B2 | 5/2006 | Chu | |
| 7,524,281 B2 | 4/2009 | Chu et al. | |
| 7,842,046 B1 * | 11/2010 | Nakao | 606/144 |
| 2003/0233107 A1 * | 12/2003 | Gellman et al. | 606/144 |
| 2004/0181243 A1 | 9/2004 | Chu et al. | |
| 2005/0222589 A1 | 10/2005 | Chu | |
| 2005/0283170 A1 * | 12/2005 | Battles et al. | 606/144 |
| 2006/0199994 A1 | 9/2006 | Inman et al. | |
| 2006/0206119 A1 | 9/2006 | Chu | |
| 2007/0173864 A1 | 7/2007 | Chu | |
| 2008/0082121 A1 | 4/2008 | Chu | |

(Continued)

OTHER PUBLICATIONS

Capio (TM) Suture Capturing Device, "Reach, Throw and Capture: One Step. One Device." Boston Scientific Microvasive product brochure (1998).

(Continued)

*Primary Examiner* — Charles A Marmor, II
*Assistant Examiner* — Carrie R Dorna

(57) ABSTRACT

A medical device for the delivery of pelvic floor repair implants within a pelvic region of a body includes a handle, an elongated shaft member, and a head. A method of delivering a pelvic floor repair implant in a transvaginal implant procedure includes inserting and deploying at least a portion of the medical device into a pelvic region of a body.

20 Claims, 16 Drawing Sheets

(56) References Cited

U.S. PATENT DOCUMENTS

| | | |
|---|---|---|
| 2008/0109015 A1 | 5/2008 | Chu et al. |
| 2008/0139877 A1 | 6/2008 | Chu et al. |
| 2009/0105743 A1 | 4/2009 | Chu |
| 2009/0171139 A1 | 7/2009 | Chu |
| 2009/0171140 A1 | 7/2009 | Chu |
| 2009/0171142 A1 | 7/2009 | Chu |
| 2009/0171143 A1 | 7/2009 | Chu et al. |
| 2009/0192540 A1 | 7/2009 | Chu et al. |
| 2009/0312772 A1 | 12/2009 | Chu |
| 2010/0137887 A1* | 6/2010 | Crockett et al. ............... 606/144 |
| 2011/0105836 A1* | 5/2011 | Miller ............................ 600/37 |

OTHER PUBLICATIONS

Capio (TM) CL, "Transvaginal Suture Fixation to Cooper's Ligament for Sling Procedures," Boston Scientific Microvasive product brochure (2000).

Pinnacle (TM), "Pelvic Floor Repair Kit—Anterio/Apical," Boston Scientific Microvasive product brochure (2008).

Pinnacle (R) Posterior, "Pelvic Floor Repair Kit, Level I and Level II Support, Eliminates Blind Trocar Passes," Boston Scientific Microvasive product brochure (2009).

Uphold (TM) "Vaginal Support System," Boston Scientific Microvasive product brochure (2009).

International Search Report and Written Opinion for PCT/US2011/031754, dated Nov. 30, 2011 (15 pages).

* cited by examiner

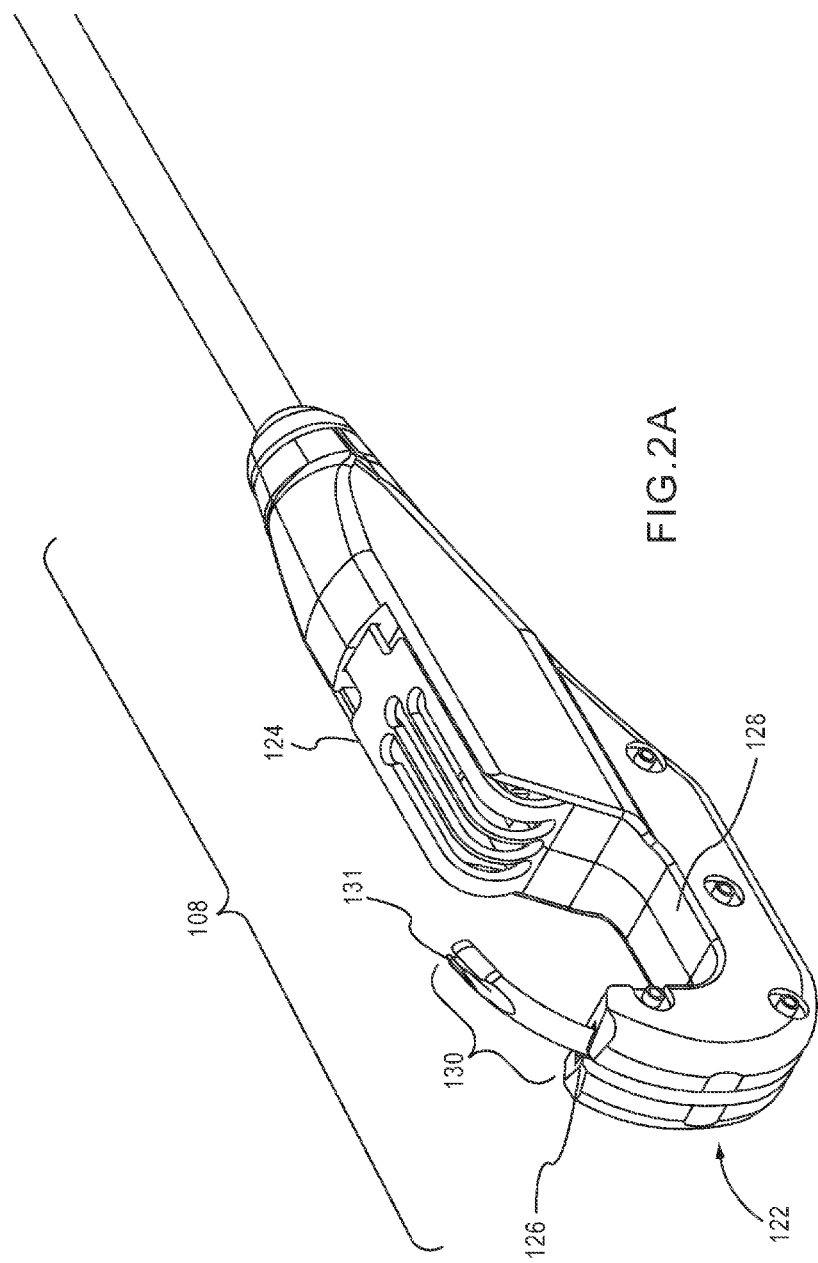

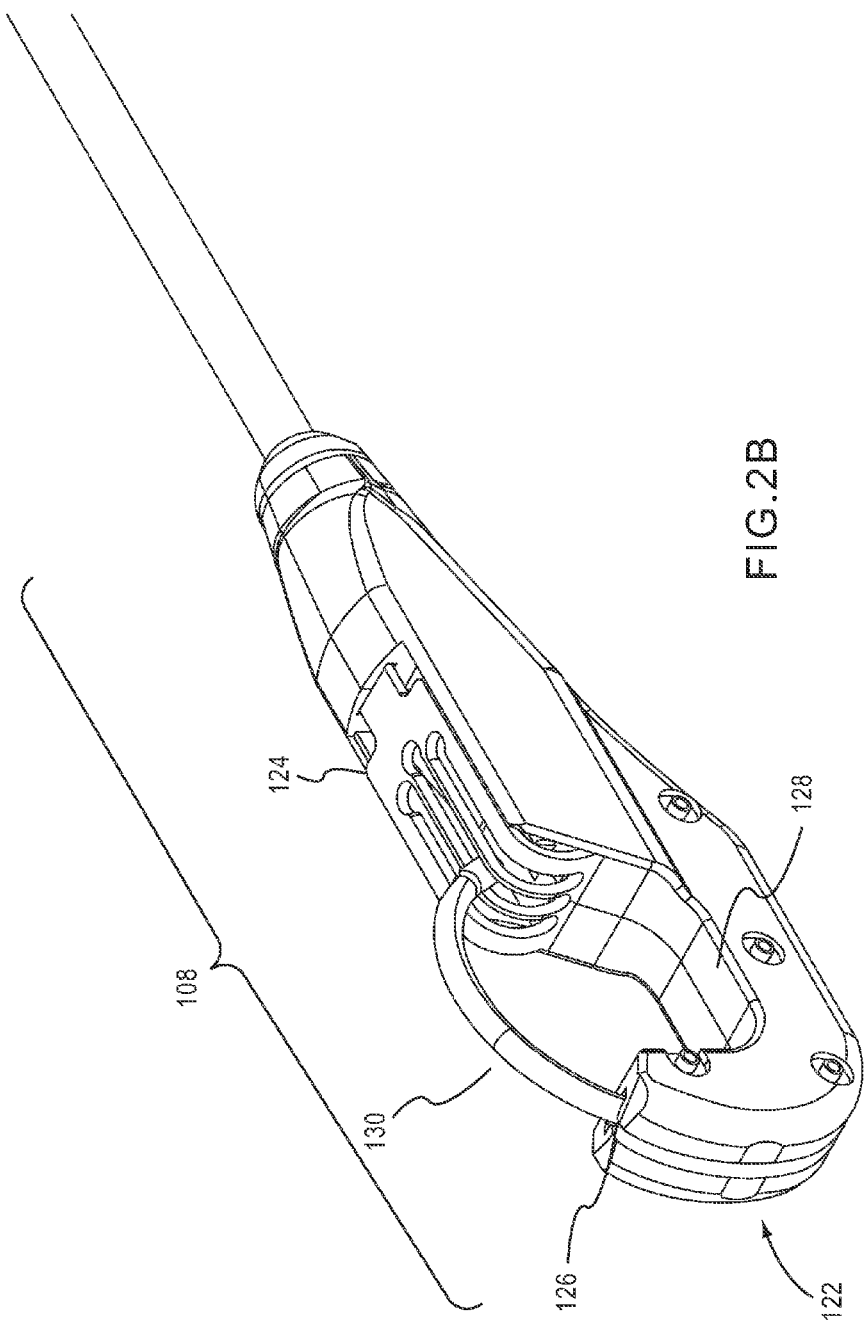

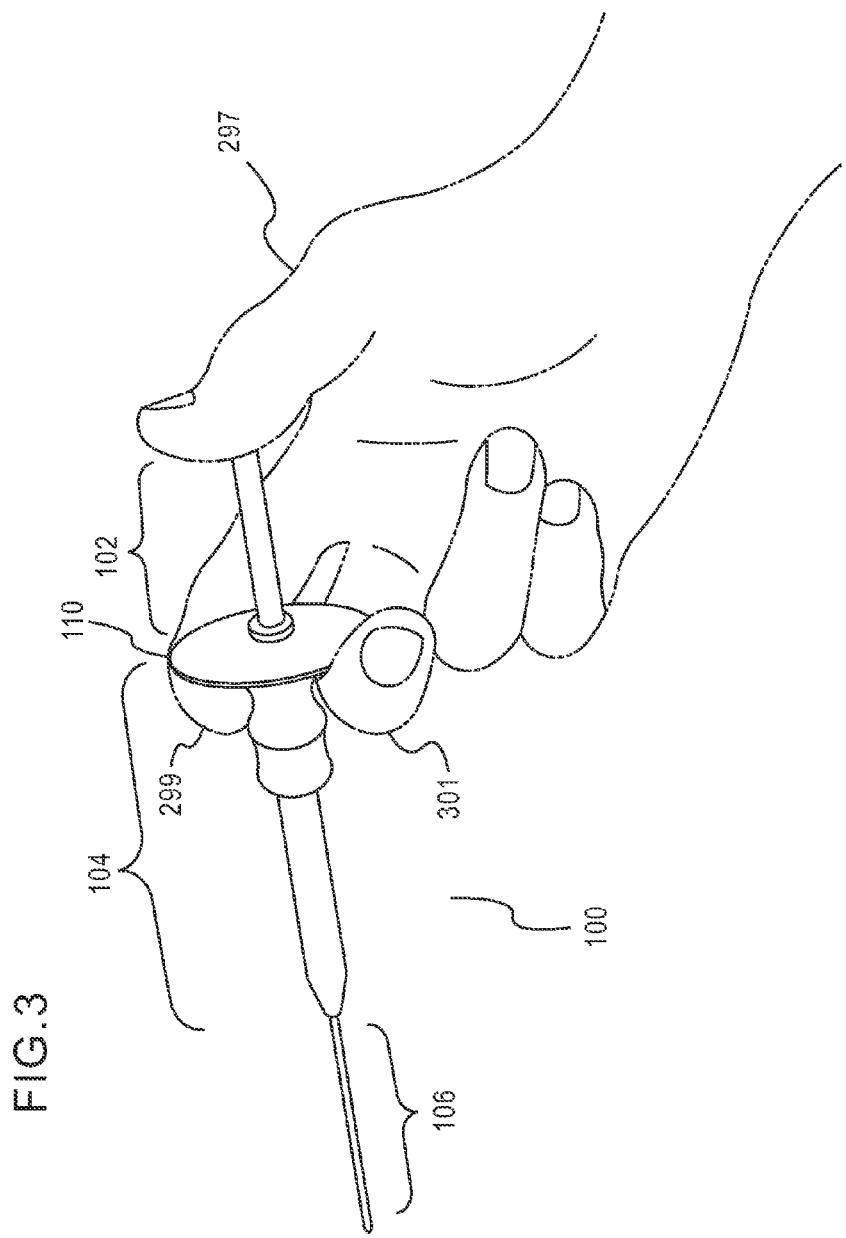

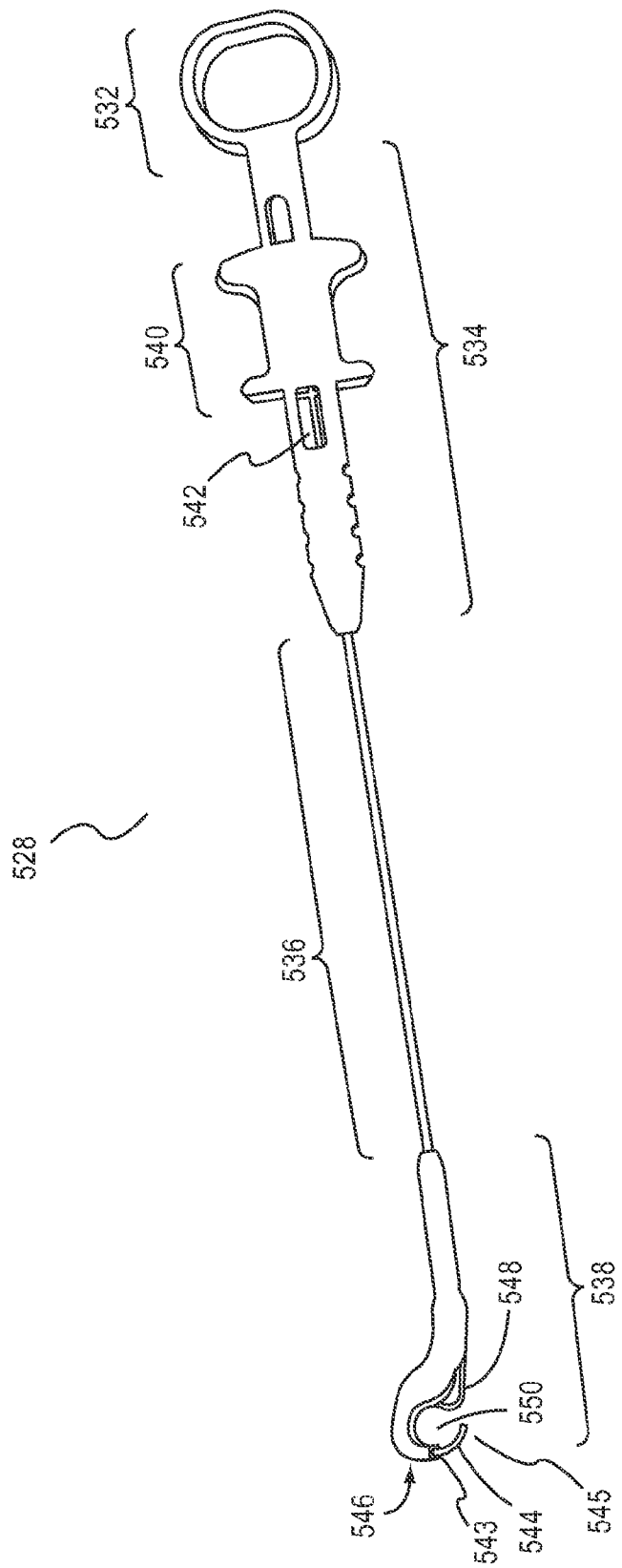

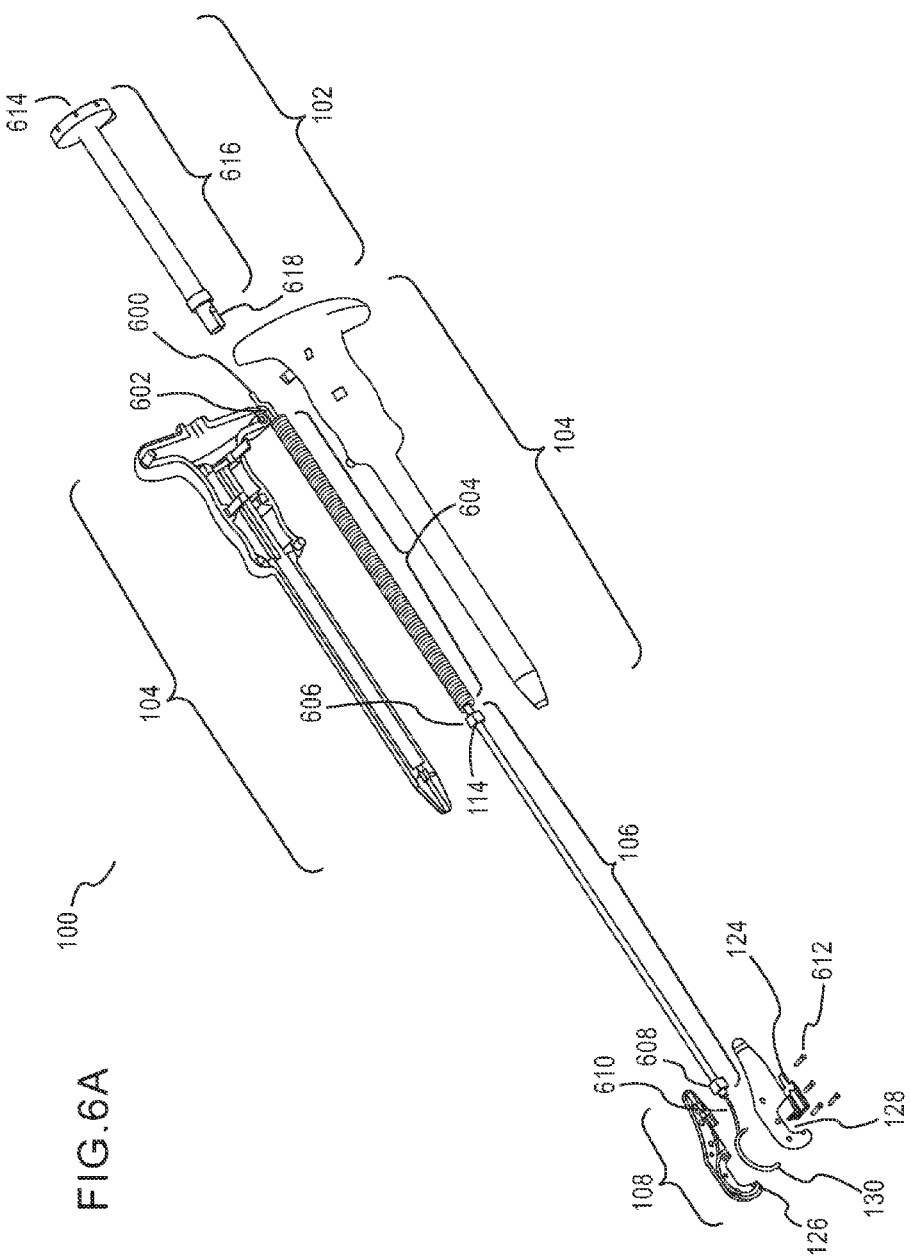

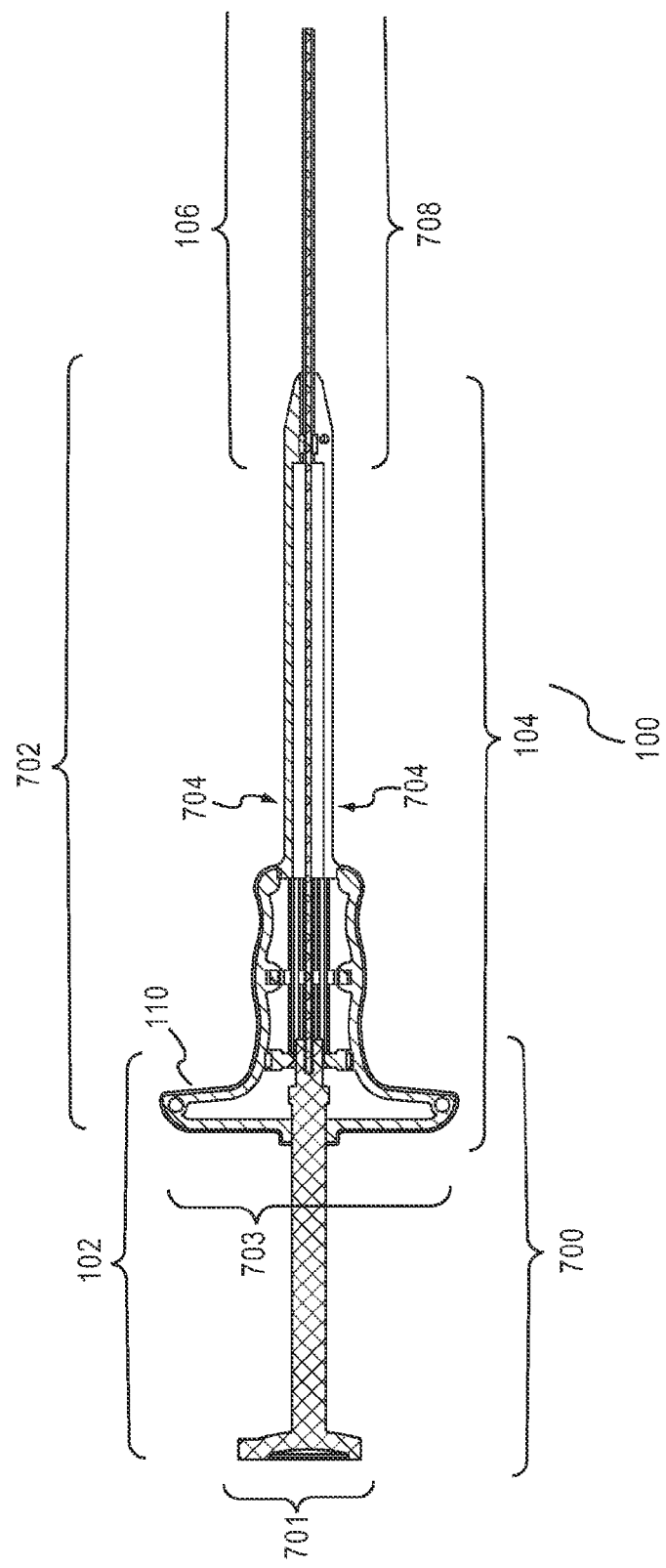

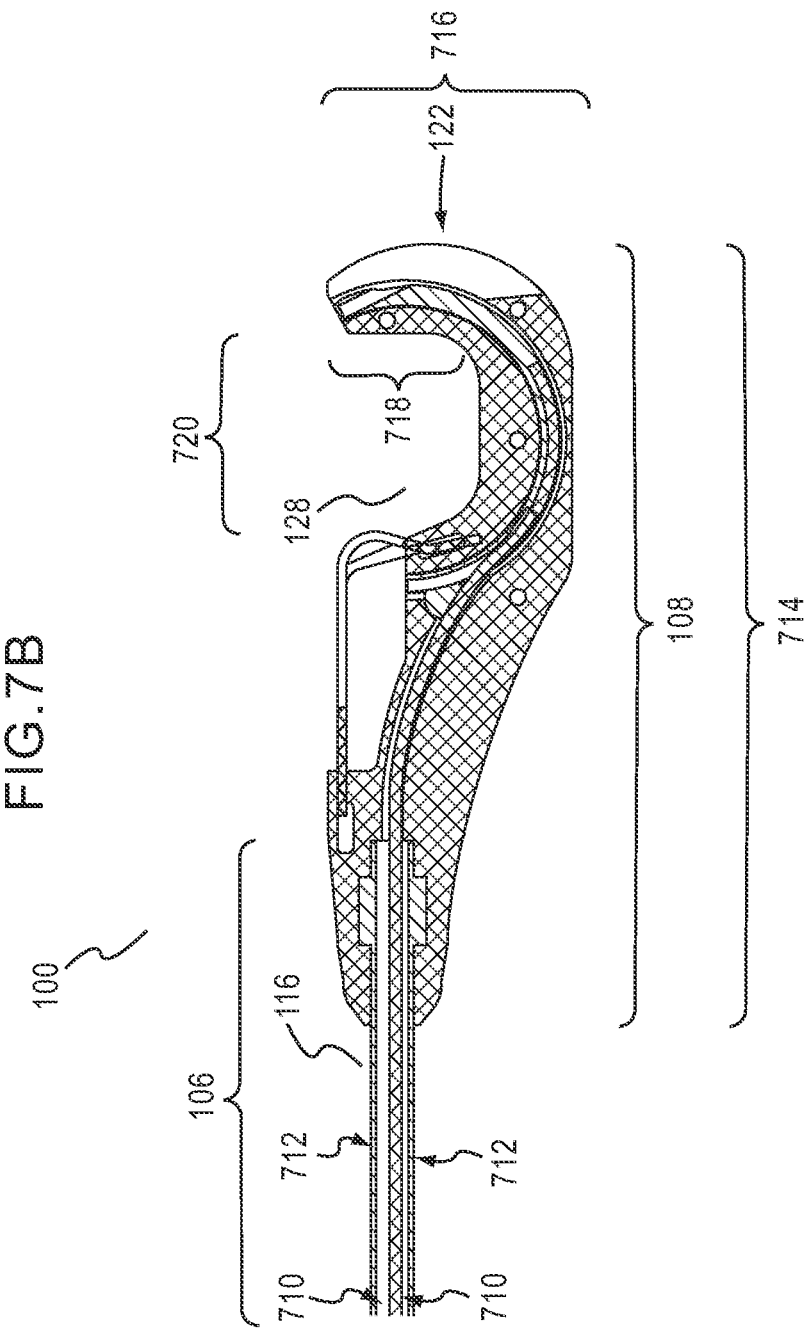

ic pelvic floor repair and/or other implants, and more particu-
DELIVERING PELVIC FLOOR REPAIR IMPLANTS

CROSS-REFERENCE TO RELATED CASE

This claims priority to and the benefit of Provisional U.S. Patent Application Ser. No. 61/330,227, filed Apr. 30, 2010, the entirety of which is incorporated herein by reference.

TECHNICAL FIELD

The invention relates to devices and methods for delivering pelvic floor repair and/or other implants, and more particularly, to minimally invasive devices and methods for delivering implants or sutures to a pelvic region of a body of a patient.

BACKGROUND INFORMATION

The delivery of a pelvic floor repair (PFR) implant is typically an invasive surgical procedure. For this surgical procedure, a large dissection can be required within the pelvic region of the human body to deliver a PFR implant.

Some commercially available medical devices are limited by the manner in which they access the pelvic region of the human body. For example, such devices typically cannot be easily manipulated to access difficult areas within the pelvic region. In addition, these devices are generally cumbersome and rigid, and therefore they do not provide the maneuverability necessary to perform a PFR implant surgical procedure in a less invasive manner.

SUMMARY OF THE INVENTION

The invention relates to improvements in medical devices, including suturing devices and devices for use in the delivery of PFR and/or other implants. A medical device according to the invention is less invasive and more manipulatable relative to existing devices in the placement of PFR and/or other implants within a pelvic region of a human body. This is accomplished, for example, by devices according to the invention having reduced profile components compared to existing devices. A medical device according to the invention allows an operator to make a minimum dissection profile within a pelvic region such that the medical device may be inserted into the pelvic region to deliver a PFR and/or other implant in a less invasive manner while providing the patient with an expedited healing process. In contrast to existing commercial devices which require large dissection profiles of a pelvic region to deliver PFR implants, the dissection profile required by devices according to the invention are significantly smaller, such as equal or about equal to the diameter of an operator's finger, the profile of the medical device, or the profile of the PFR implant. A device according to the invention also can be used to deliver one or more sutures.

In one aspect, the invention relates to a medical device for use in a transvaginal implant procedure. The medical device includes a handle, an elongated shaft member, and a head. The handle has a proximal end and a distal end. The handle also includes an actuator that is configured to be manipulated by an operator of the medical device. The elongated shaft member of the medical device defines a lumen that extends from the distal end of the handle. The elongated shaft member has a diameter that is minimally greater than a diameter of a wire form that extends longitudinally within the elongated shaft member. The elongated shaft member extends along a longitudinal axis when the elongated shaft member is disposed in a straight or a substantially straight configuration. The head of the medical device extends over a distal end of the elongated shaft member. The head has a length that is measured along the longitudinal axis of the elongated shaft member. The head also has a maximum width that is measured in a first direction that is transverse to the longitudinal axis of the elongated shaft member. In addition, the head has a thickness that measured in a second direction that is perpendicular to the first direction. The length of the head is greater than the maximum width of the head. Further, the maximum width of the head is greater than the thickness of the head. The thickness of the head is also greater than the diameter of the elongated shaft member. The head also includes a needle carrier. The needle carrier is configured to receive a needle that can be coupled to a suture or to a portion of a pelvic floor repair implant. The head further includes a needle catch and a needle exit port. At least a portion of the needle carrier exits the needle exit port when the operator manipulates the actuator. The needle catch is configured to receive and retain the needle carried by the needle carrier.

In one embodiment according to this aspect of the invention, the handle of the medical device has a length that extends off at an angle from the length of the handle, such as a 90° angle. The handle can also include a spring that is disposed between the proximal end and the distal end of the handle. The actuator can be configured to cause compression of the spring when the operator of the medical device manipulates the actuator.

The elongated shaft member can be deflectable off the longitudinal axis by manipulation by the operator. The elongated shaft member can have an outer surface that is exposed such that the operator can touch the outer surface while manipulating the actuator during the transvaginal implant procedure.

The wire form of the medical device can move longitudinally within the elongated shaft member to cause the needle carrier to exit the needle exit port when the operator depresses the actuator. The proximal end of the wire form can be coupled to the actuator. The actuator could include a plunger or a trigger. The elongated shaft member can be deflectable into a shape that is retained during use of the medical device. The head of the medical device can be rotatable relative to the longitudinal axis of the elongated shaft member. The head of the medical device can include an opening for receiving tissue of a patient's body, and that opening can include a substantially C-shaped configuration. The head can also include a channel in which a needle carrier is disposed. The needle carrier can be movable within the channel when the operator manipulates the actuator of the medical device. The elongated shaft member of the medical device can be made of one or more shape memory materials.

In a second aspect, the invention relates to a medical device for use in a transvaginal implant procedure. The medical device according to the second aspect of the invention also includes a handle, an elongated shaft member, and a head. The handle includes a spool member and a ring member. The spool member is configured for receiving at least two fingers of an operator of the medical device and the ring member is configured for receiving a thumb of the operator. The elongated shaft member of the medical device defines a lumen that extends from the distal end of the handle. The elongated shaft member has a diameter that is minimally greater than a diameter of a wire form that extends longitudinally within the elongated shaft member. The elongated shaft member extends along a longitudinal axis when the elongated shaft member is disposed in a straight or a substantially straight configuration. The head of the medical device extends over a distal end of the elongated shaft member. The head has a length that is measured along the longitudinal axis of the elongated shaft member. The head also has a maximum width that is measured in a first direction that is transverse to the longitudinal axis of the elongated shaft member. In addition, the head has a thickness that measured in a second direction that is perpendicular to the first direction. The length of the head is greater than the maximum width of the head. Further, the maximum width of the head is greater than the thickness of the head. The thickness of the head is also greater than the diameter of the elongated shaft member. The head includes a needle carrier. The needle carrier is configured to receive a needle that can be coupled to a suture or to a portion of a pelvic floor repair implant. The head further includes a needle catch and a needle exit port. At least a portion of the needle carrier exits the needle exit port when the operator manipulates the handle. The needle catch is configured to receive and retain the needle carried by the needle carrier.

In one embodiment according to this aspect of the invention, the wire form of the medical device can move longitudinally within the elongated shaft member to cause the needle carrier to exit the needle exit port when the operator depresses the handle. The elongated shaft member can be deflectable off the longitudinal axis by manipulation by the operator. The elongated shaft member can have an outer surface that is exposed such that the operator can touch the outer surface while manipulating the handle during the transvaginal implant procedure. The head of the medical device can include a channel in which a needle carrier is disposed. The needle carrier can be movable within the channel when the operator manipulates the handle of the medical device.

In a third aspect, the invention relates to a method of delivering a pelvic floor repair implant. The method includes providing a medical device, such as one of the medical devices described above, inserting a needle coupled to a portion of a pelvic floor repair implant into the medical device, dissecting a patient's body to create an opening to a pelvic region of the patient's body, inserting the elongated shaft member and the head of the medical device through the opening to the pelvic region, manipulating the head and the opening of the head onto a ligament within the pelvic region, and deploying the needle carrier out of the needle exit port of the medical device and pushing the needle and the pelvic floor repair implant through the ligament.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same or similar parts throughout the different views. Also, the drawings are not necessarily to scale, emphasis instead generally being placed upon illustrating the principles of the invention.

FIG. 2A is an exploded perspective view of the needle carrier exiting a needle exit port of the medical device.

FIG. 2B is a perspective view of the head of the medical device of FIG. 1B.

FIG. 3 is a perspective view of the handle portion being held by an operator of the medical device.

FIG. 5B is a plan view of another embodiment of the medical device of FIG. 1A.

FIG. 6A is a broken view of the medical device of FIG. 1A.

FIG. 7A is a cross sectional view of the actuator, the handle, and the elongated shaft member of the medical device of FIG. 1A.

FIG. 7B is a cross sectional view of the elongated shaft member and the head of the medical device of FIG. 1A.

DESCRIPTION

In general, the invention relates to improvements in medical devices, including suturing devices and devices for use in the delivery of pelvic floor repair (PFR) implants. Various devices are disclosed in U.S. Pat. No. 7,041,111 and U.S. Pat. Pub. Nos. 2004/0181243 and 2008/0109015, each of which is incorporated by reference herein in its entirety. Further, the invention generally relates to improvements to existing devices to make them less invasive and more manipulative for the placement of PFR and/or other implants through transvaginal approaches. Some commercially available devices are Boston Scientific Corporation devices such as the Capio® CL Transvaginal Suture Capturing Device, the Capio® Open Access and Standard Suture Capturing Device, the Pinnacle® Pelvic Floor Repair Kit—Anterior/Apical/Posterior, and the Uphold™ Vaginal Support System.

Figure 1A:
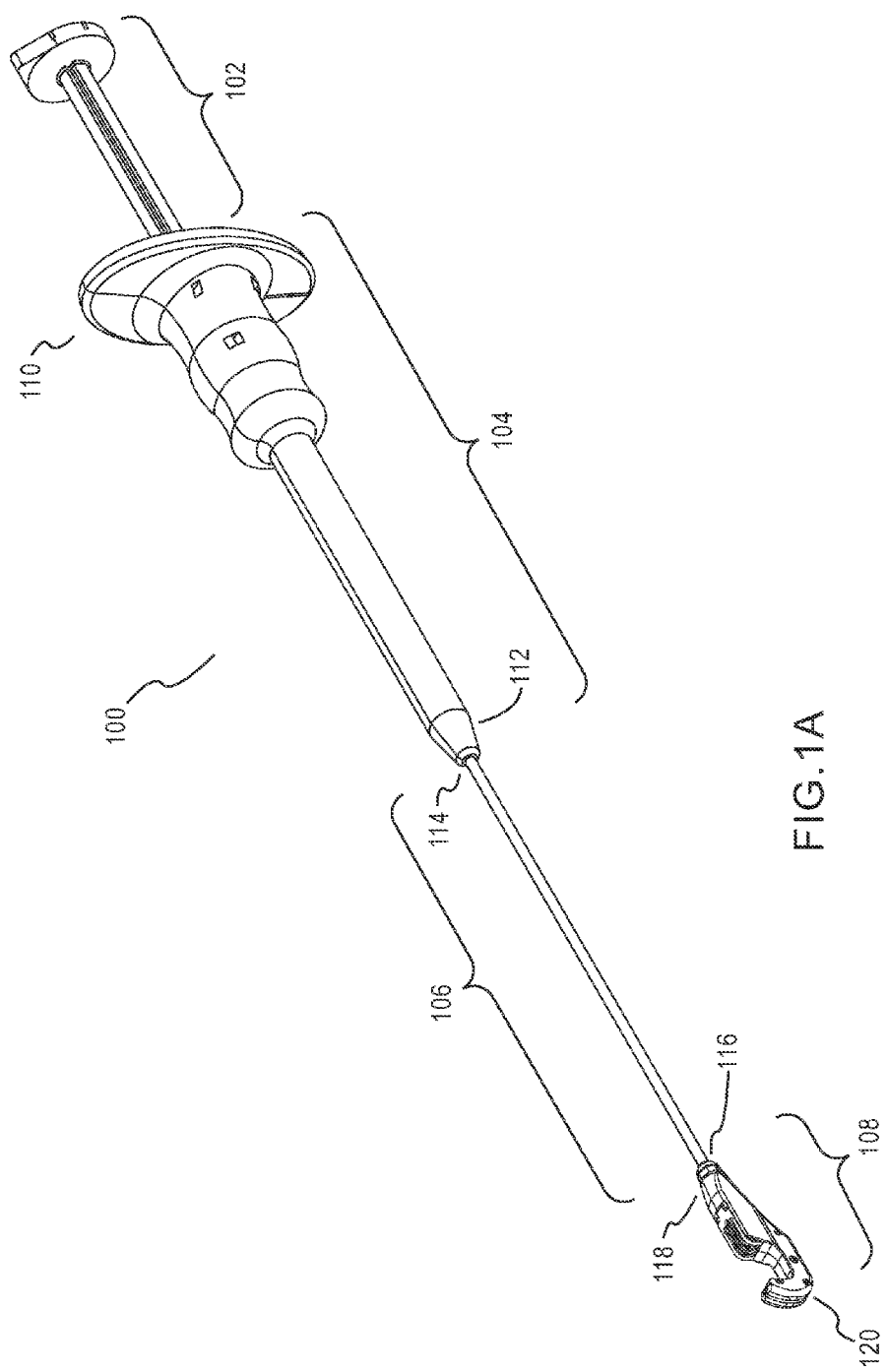
FIG. 1A is a perspective view of an embodiment of a medical device for use in delivering a PFR and/or other implant.

Referring to FIG. 1A, in one embodiment according to the invention, a medical device 100 includes an actuator 102, a handle 104, an elongated shaft member 106, and a head 108. A portion of the actuator 102 is slidably disposed within a proximal end 110 of the handle 104, and a portion of the actuator 102 extends out of the proximal end 110 of the handle 104.

A proximal end 114 of the elongated shaft member 106 extends into and is partially disposed within a distal end 112 of the handle 104. A distal end 116 of the elongated shaft member 106 extends into and is partially disposed within a proximal end 118 of the head 108. The elongated shaft member 106 is capable of being deflected into a shape and retaining the shape during use. The elongated shaft member 106 may instead be deflectable from a straight configuration such that it returns back to a straight or substantially straight configuration when the deflecting force is removed or reduced. The proximal end 118 of the head 108 includes a substantially flat configuration. A distal end 120 of the head 108 includes a substantially curved configuration.

Figure 1B:
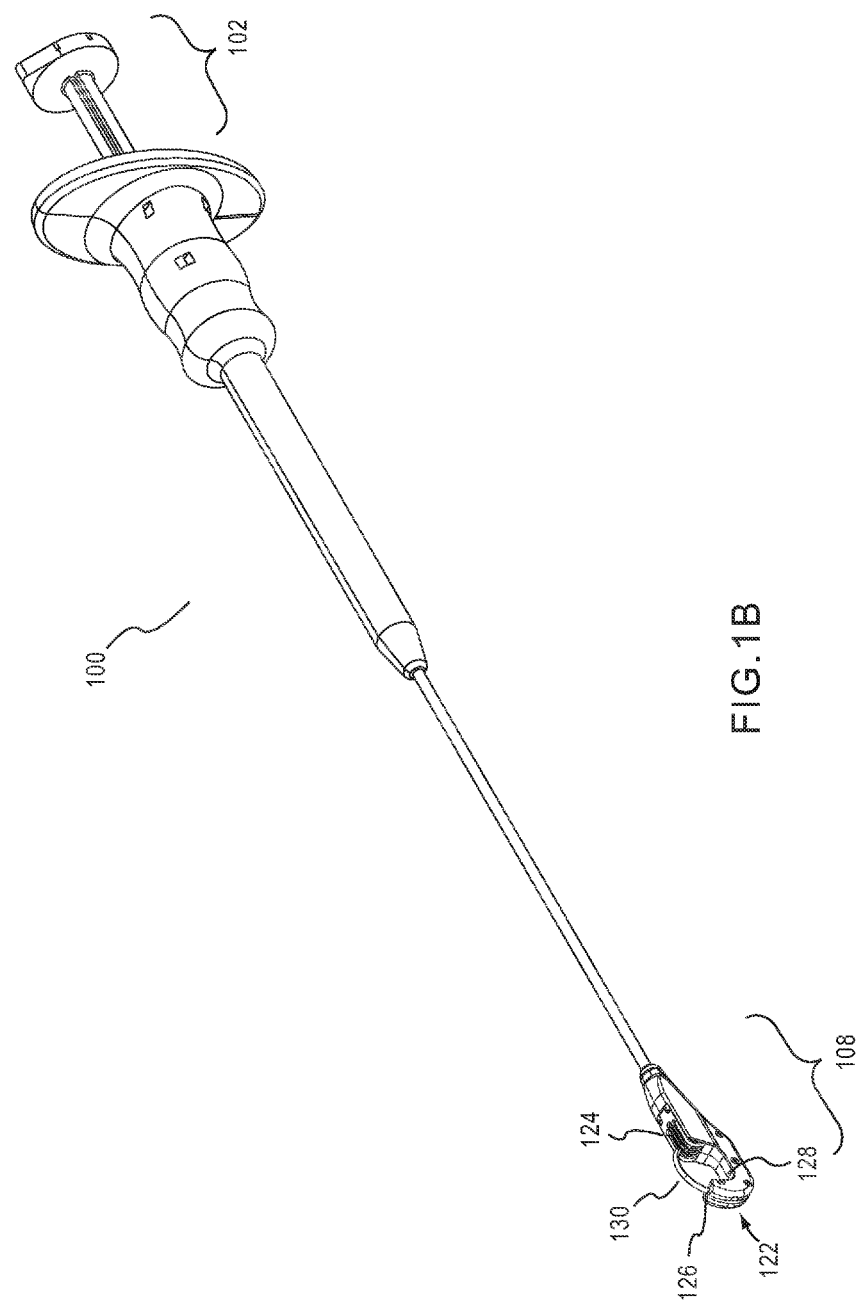
FIG. 1B is a perspective view of the medical device after a needle catch has received a needle carrier.

Referring to FIGS. 1B, 2A, and 2B, the head 108 of the medical device 100 of FIG. 1A includes a curved portion 122, a needle catch 124, a needle exit port 126, an opening 128, and a needle carrier 130. The opening 128 is configured to receive tissue of a patient's body. In one embodiment, the opening 128 includes a substantially C-shaped configuration. The needle carrier 130 defines a distal receiving slot 131. An operator (such as a physician or other medical personnel) manipulates the needle carrier 130 by depressing the actuator 102, such that the needle carrier 130 slidably moves through the needle exit port 126 as the actuator 102 is depressed. The operator continues to depress the actuator 102 until the needle carrier 130 enters the needle catch 124. The needle carrier 130 may be used to transvaginally deliver a PFR and/or other implant or sling. The needle carrier 130 may instead be used for suture placement. Various existing devices utilize a similar mechanism in order to deploy the needle carrier 130, such as the device disclosed in U.S. Pat. Pub. No. 2004/0181243.

Figure 2C:
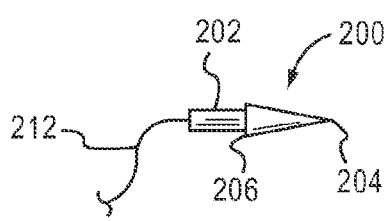
FIG. 2C is a plan view of a needle for use in the medical device.
Figure 2D:
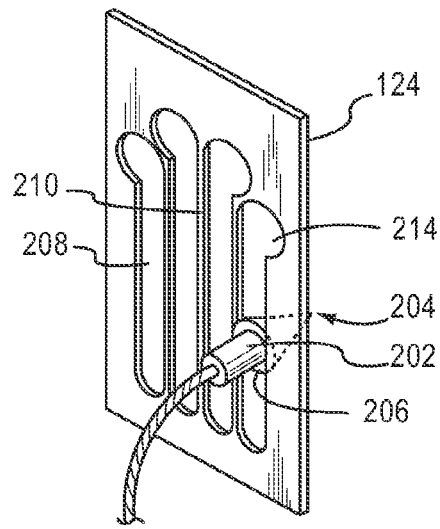
FIG. 2D is a perspective view of a needle catch.

Referring to FIGS. 2A, 2B, and 2C, a needle 200 can be disposed within the receiving slot 131 of the needle carrier 130. The needle 200 includes a shaft 202, a tip 204, a formed shoulder 206, and a filament 212. The filament 212 may be, for example, a suture, a wire, or other device to be delivered to the body of a patient. The needle 200 is held within the needle carrier 130 by a frictional fit between the shaft 202 and the receiving slot 131. The needle 200 may be configured for use with various configurations of the needle catch 124. The needle 200 may be dart-shaped, ring-shaped, or cone-shaped. The filament 212 could be attached to an implant and/or sling, which is to be delivered to the body of the patient.

Referring to FIGS. 1A, 1B, 2A, 2B, 2C, and 2D, an operator of the medical device 100 can depress the actuator 102 to slidably move the needle carrier 130 out of the needle exit port 126. If the operator continues to depress the actuator 102, the needle 200 and enters the needle catch 124. The needle catch 124 includes openings 208, successive ribs 210, and enlarged portions 214. In one embodiment, the needle catch 124 receives the needle 200 through the opening 208, and the ribs 210 deflect slightly to allow the needle 200 to pass through. After the formed shoulder 206 has passed through the ribs 210 and the needle carrier 130 has been withdrawn (by releasing the actuator 102), thereby pulling the needle 200 out of the receiving slot 131 and releasing the needle 200 from the needle carrier 130, the ribs 210 spring back to their original position defining the openings 208. The openings 208 are chosen to be smaller in dimension than the formed shoulder 206. This causes the needle catch 124 to retain the needle 200, because, due to the flat rear surface of the shoulder 206, the needle 200 cannot pass back through the opening 208 when the needle carrier 130 retracts. When it is necessary to remove the needle 200 from the needle catch 124, the needle 200 may be removed via the enlarged portion 214. The enlarged portion 214 is sized to allow the formed shoulder 206 to pass through without resistance. The needle catch 124 is preferably constructed of thin stainless steel of high temper, such as ANSI 301 full hard. The needle catch 124 may be fabricated by means of stamping, laser machining, or chemical etching.

Figure 2E:
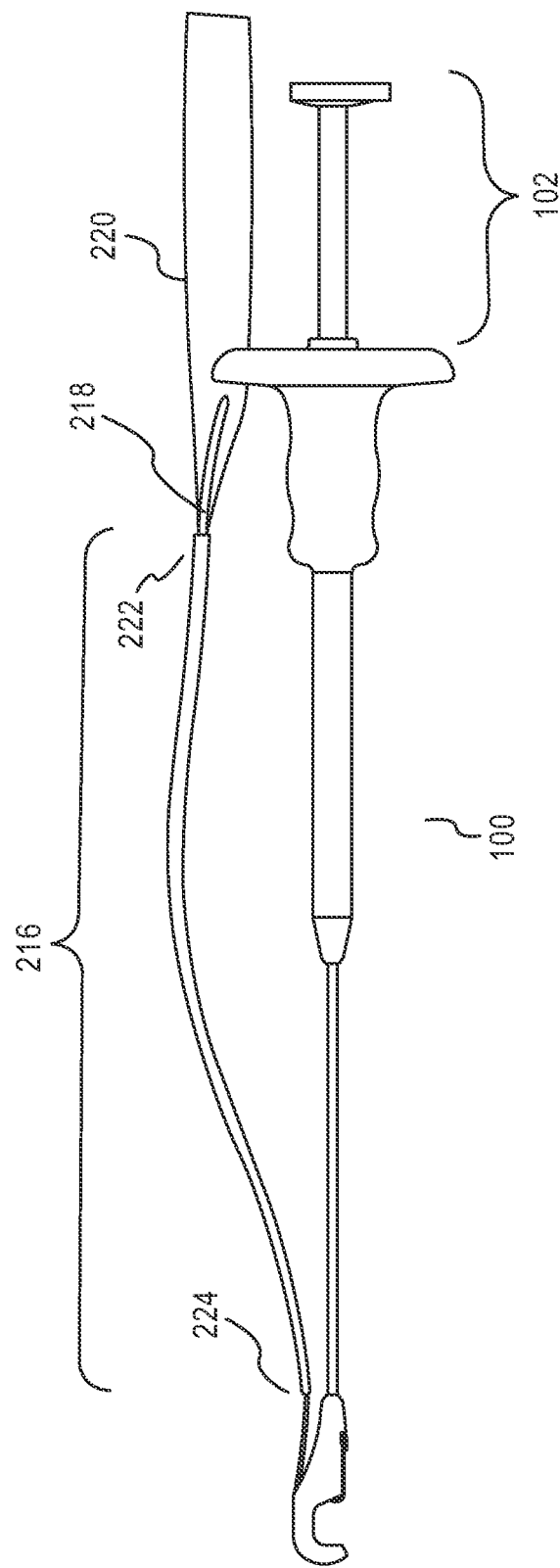
FIG. 2E is a plan view of the medical device similar to FIG. 1A but including an elongated lumen member for delivering a sling.

Referring to FIG. 2E, the medical device 100 of FIG. 1A can be used to deliver an elongated lumen member 216 that is a transport for a sling 218 encased within a transparent lumen 220. The elongated lumen member 216 defines an opening that is tapered from a proximal end 222 to a distal end 224. The sling 218 extends through and out of the proximal end 222 of the elongated lumen member 216. An operator could depress the actuator 102 to cause the sling 218 to pass through the elongated lumen member 216, and the sling 218 could then be pulled through a tissue within a pelvic region of a patient. It is known to deliver a suture and a sling (or other implant) into the body of a patient as indicated by the following published U.S. patent applications, all of which are incorporated herein by reference in their entirety: 2007/0173864; 2008/0082121; 2008/0139877; 2009/0192540; and 2009/0312772. The sling 218 can be a pelvic floor repair (PFR) implant as described hereinbefore and hereafter.

Referring to FIG. 3, an operator may hold the proximal end 110 of the handle 104 of the medical device 100 of FIG. 1A with two fingers, such as a forefinger 299 and a middle finger 301, and may depress the actuator 102 with a thumb 297. The actuator 102 thus comprises a plunger. However, in other embodiments, the actuator may be configured as a trigger or other configuration. The operator may use either hand or both hands to operate the medical device 100. The elongated shaft member 106 includes an outer surface that is exposed such that the operator can touch the outer surface while manipulating the actuator during the transvaginal implant procedure. The operator's forefinger of one hand could be used to guide the outer surface of the elongated shaft member 106, while the other hand of the operator could be used to hold the proximal end 110 of the handle 104 and depress the actuator 102. The handle 104 may be configured such that it is longer or shorter in length.

Figure 4A:
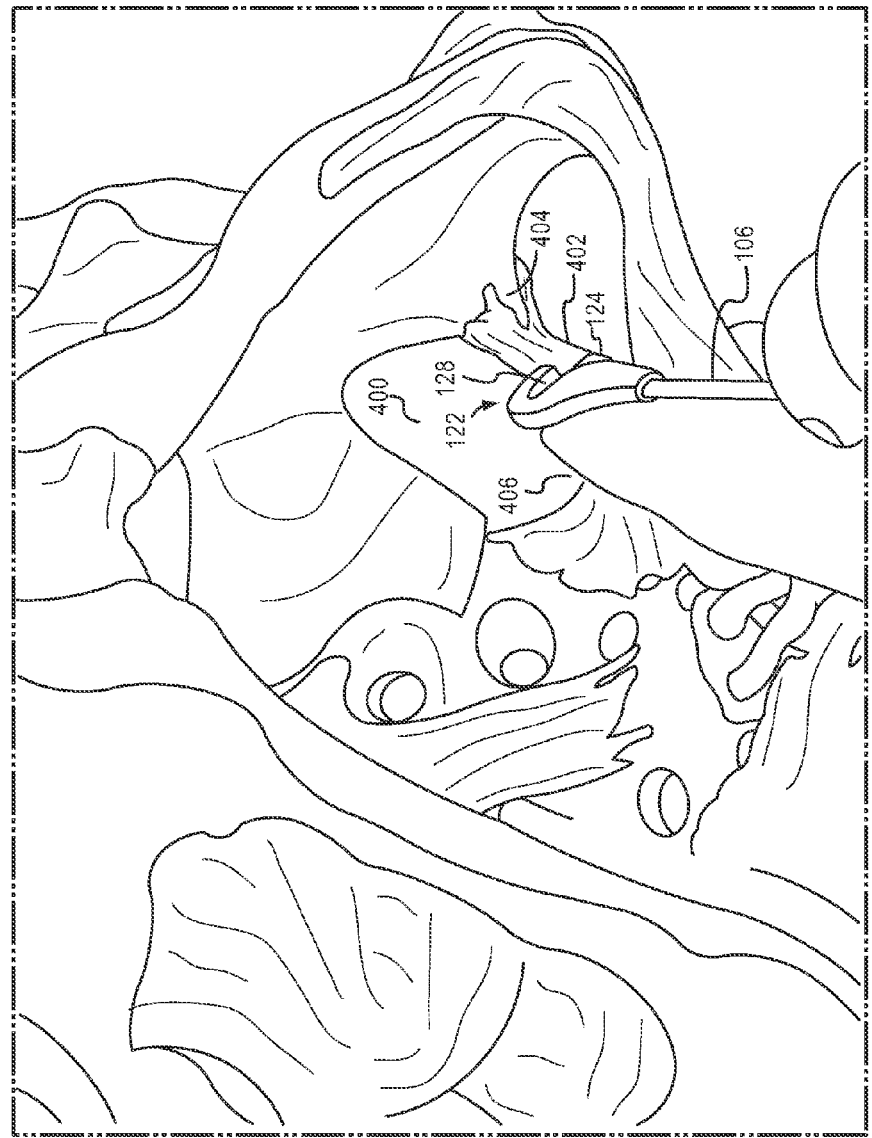
FIG. 4A is a perspective view of the medical device in use during a transvaginal implant procedure.
Figure 4B:
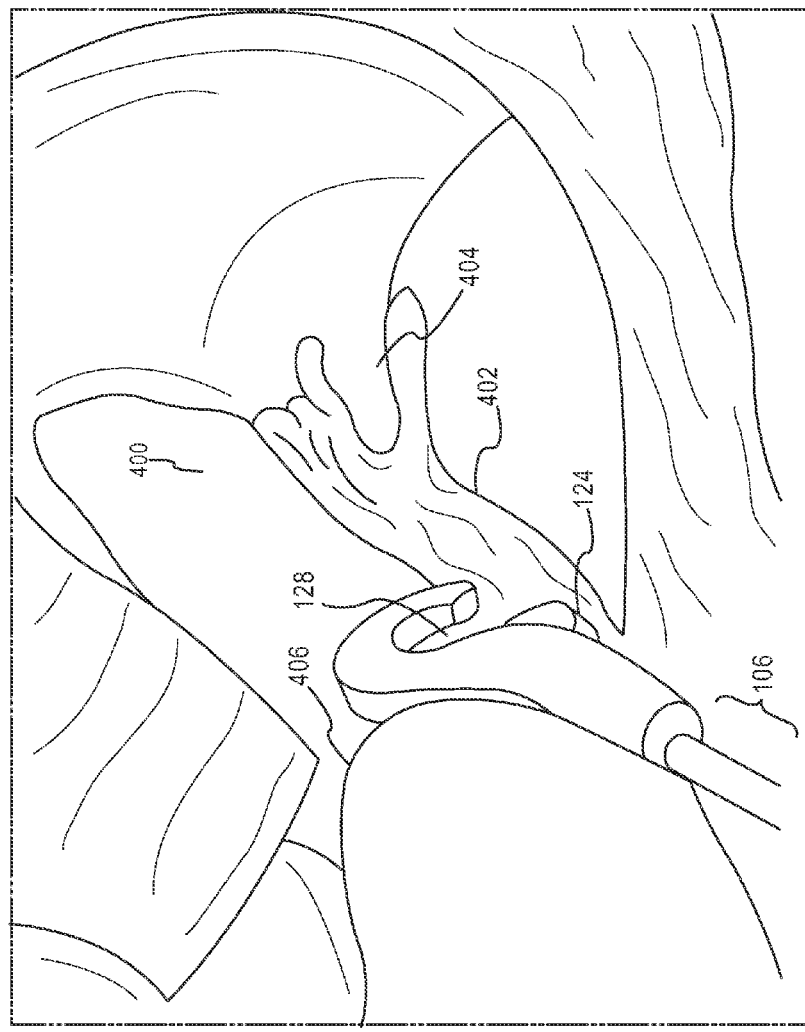
FIG. 4B is an exploded perspective view of the medical device of FIG. 4A.

Referring to FIGS. 4A and 4B, the medical device 100 of FIG. 1A can be inserted into a patient's pelvic region 400. The pelvic region 400 includes a sacrospinous ligament (SSL) 402 and an arcus tendineae fascia pelvis (ATFP) 404. Once the opening 128 is placed onto the SSL 402, the operator may place his/her finger 406 directly on top of the curved portion 122 to position the head 108 (FIG. 1B) prior to depressing the actuator 102 (FIG. 1B).

The medical device 100 of FIG. 1A can be used to pass at least a portion of a PFR and/or other implant through a tissue within the patient's pelvic region 400 to secure the implant in place. The medical device 100 may be used as part of palpation by an operator prior to delivering a PFR implant. The ATFP 404 may be the first landmark that the operator feels for after dissection of the pelvic region 400. Dissection of the pelvic region 400 may be required to access the SSL 402 for placing the PFR implant. The dissection profile required as part of palpation by an operator may be equal to the diameter of the operator's finger, the profile of the medical device 100, or the profile of the PFR implant. The profile of the medical device 100 may minimize the dissection profile within the patient's pelvic region 400. A smaller dissection profile typically provides the patient with an expedited healing process. Upon locating the ATFP 404, the operator may move his/her finger 406 onto the SSL 402. The operator may then insert the head 108 into the patient's pelvic region 400 and slide the elongated shaft member 106 along his/her finger 406 towards the SSL 402, so that the needle exit port 126 (FIG. 1B) may deliver an implant to the SSL 402. The operator could then depress the actuator 102 using his/her finger of the other hand, thereby causing the needle carrier 130 (FIG. 1B) to extend out of the needle exit port 126 and push the needle 200 (FIG. 2C) through the SSL 402. As the needle 200 is pushed through the SSL 402, the needle 200 pulls the implant through the SSL 402. As the operator continues to depress the actuator 102, the needle carrier 130 continues to advance out of the needle exit port 126 and directs the needle 200 toward the needle catch 124. The operator continues to depress the actuator 102 until the needle 200 contacts and becomes captured by the needle catch 124.

The operator of the medical device 100 may instead insert the head 108 into the patient's pelvic region 400 before inserting his/her finger 406 to locate the ATFP 404. This procedure may be used to minimize the required dissection into the patient's pelvic region 400. The operator may also insert the head 108 simultaneously with his/her finger 406 into the patient's pelvic region 400. Additionally, the operator may slide the head 108 underneath his/her finger 406 towards the SSL 402. Further, the operator may utilize a scope having a diameter less than the diameter of the operator's finger 406 for visual guidance of the head 108 towards the ATFP 404 and the SSL 402.

Figure 4C:
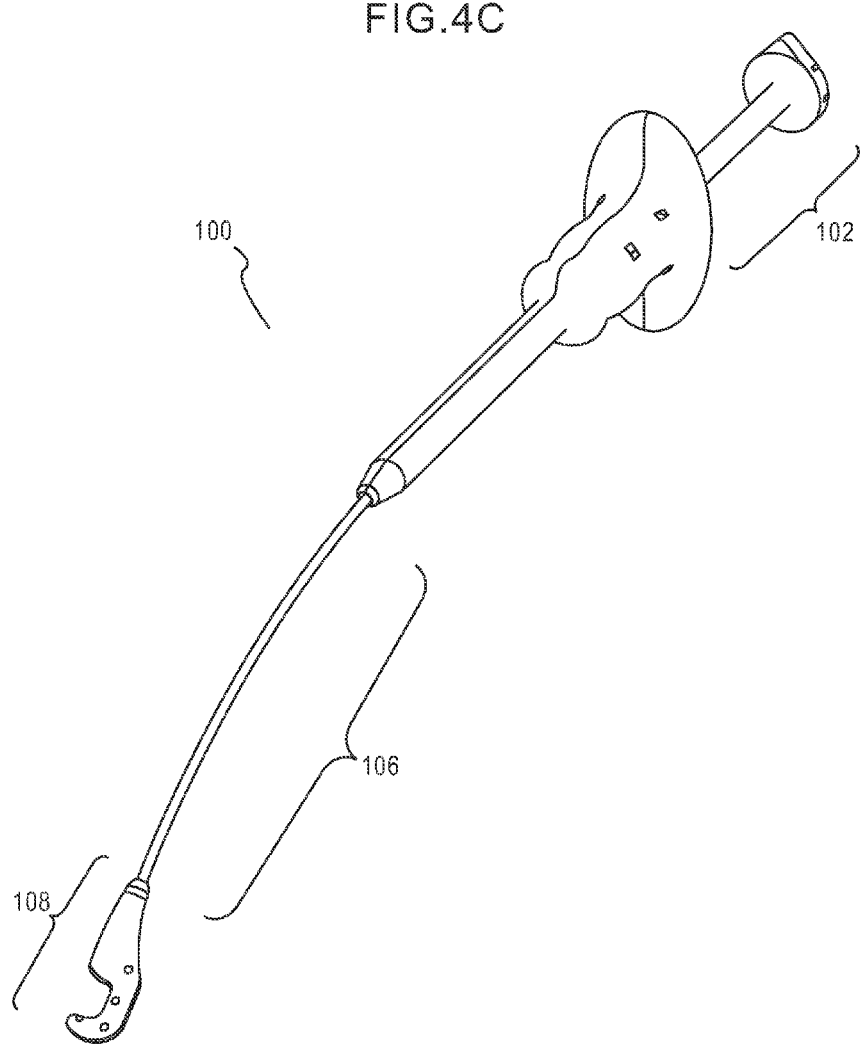
FIG. 4C is a perspective view of the elongated shaft member of the medical device of FIG. 1A being deflected off the longitudinal axis.

Referring to FIG. 4C, an operator may deflect the elongated shaft member 106 of the medical device of FIG. 1A in order to facilitate the access of difficult locations within a patient's pelvic region. In one embodiment, the operator may deflect the elongated shaft member 106 into a bent shape to suit the specific patient's needs or to efficiently orient the elongated shaft member 106 to reach the desired location of use. The elongated shaft member 106 maintains its shape during use. The elongated shaft member 106 is not limited to one shape and can be repeatedly bent into any number of shapes, if necessary. The elongated shaft member 106 may be re-bent, re-shaped, or bent as a compounded curve, if necessary. The components of the medical device 100 are sized such that the actuator 102 will not bind when the elongated shaft member 106 and the head 108 are bent. When the elongated shaft member 106 is deflected, the components inside deflect with it. The elongated shaft member 106 may instead be semi-flexible and deflectable. The elongated shaft member 106 may be deflectable in any direction. The head 108 may also be rotatable about the longitudinal axis of the elongated shaft member 106. In one embodiment, the angle of rotation of the head 108 may be limited to about 270 degrees to prevent overwinding.

Figure 5A:
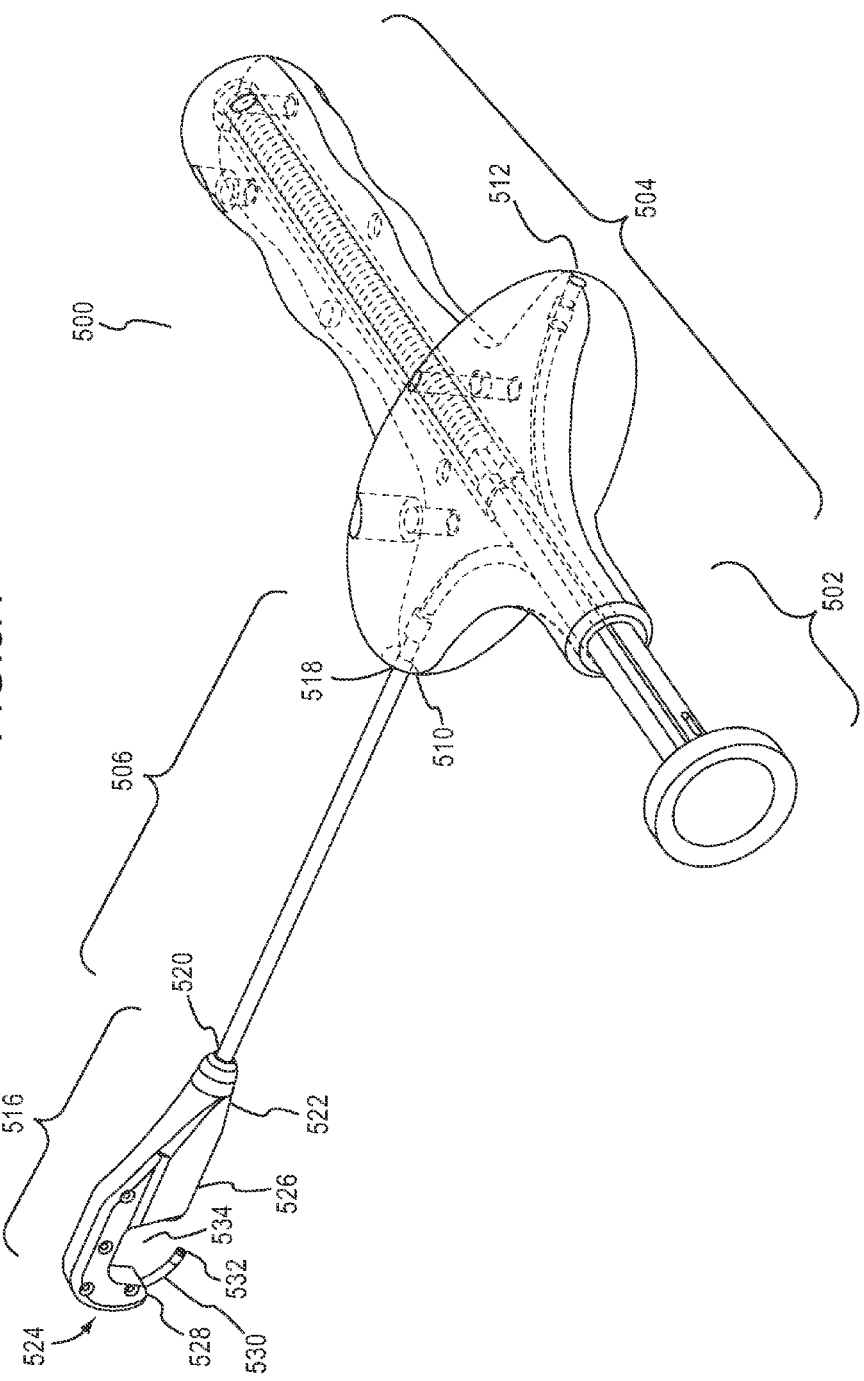
FIG. 5A is a perspective view of another embodiment of the medical device of FIG. 1A.

Referring to FIG. 5A, another embodiment according to the invention is depicted as a medical device 500 that is pistol-shaped. The medical device 500 includes an actuator 502, a handle 504, an elongated shaft member 506, a first channel 510, a second channel 512, and a head 516. As with the first embodiment described with respect to FIGS. 1A-4C, a portion of the actuator 502 is slidably disposed within the handle 504, and a portion of the actuator 502 extends out of the handle 504, but in this second embodiment, the shaft member 506 extends off at an angle, such as 90° degrees, from the side of the handle 504. A proximal end 518 of the elongated shaft member 506 extends into and is partially disposed within the first channel 510 of the handle 504. The elongated shaft member 506 could instead extend from the second channel 512 to allow right hand or left hand use of the medical device 500 by an operator. A distal end 520 of the elongated shaft member 506 extends into and is partially disposed with a proximal end 522 of the head 516. The head 516 includes a curved portion 524, a needle catch 526, a needle exit port 528, a needle carrier 530, a distal receiving slot 532, and an opening 534. Like the opening 128, the opening 534 is adapted for receiving tissue from a patient's body. In operation, the medical device 500 functions as does the medical device 100 of FIGS. 1A-4C. For example, the needle carrier 530 is deployed as the actuator 502 is depressed by an operator. The medical device 500 may be held upright, but with the operator's forefinger extended along some of the elongated shaft member 506. In addition, the elongated shaft member 506 may be deflectable in different directions in order to facilitate procedures in the pelvic region, as the shaft member 106 of the medical device 100 is deflectable.

Referring to FIG. 5B, yet embodiment according to the invention is depicted as a medical device 528. The medical device 528 includes a substantially O-shaped thumb-receiving ring member 532, a handle 534, an elongated shaft member 536, a head 538, a spool member 540, and a wire form 542. The head 538 includes a needle exit port 543, a needle carrier 544, distal receiving slot 545, a curved portion 546, a needle catch 548, and an opening 550. The distal receiving slot 545 is configured for receiving a needle. The wire form 542 moves longitudinally within the elongated shaft member 536, which causes the needle carrier 544 to exit the needle exit port 543 when the operator manipulates the handle 534. The ring member 532 is a stationary part, the spool member 540 is coupled to the wire form 542, and the wire form 542 is coupled to the needle carrier 544. An operator could insert his/her thumb into the ring member 532 and place his/her other fingers, such as the forefinger and middle finger, around the spool member 540. The operator may then extend the needle carrier 544 out of the head 538 by pushing the spool member 540 in an opposite direction from the stationary ring member 532. In order to retract the needle carrier 544 into the head 538, the operator may pull the spool member 540 towards the stationary ring member 532 such that the distance between the operator's thumb and other fingers are minimal.

In another embodiment according to the invention, the medical device 528 is configured such that wire form 542 is coupled to the ring member 532, and the spool member 540 is permanently coupled to the handle 534. The operator can depress the ring member 532 in order to deploy the needle carrier 544 from the head 538. The operator may retract the needle carrier 544 by pulling the ring member 532 in an opposite direction from the stationary spool member 540 and the handle 534.

Referring to FIG. 6A, each of the components of the medical device 100 of FIG. 1B is presented. The medical device 100 includes the actuator 102, the handle 104, the elongated shaft member 106, the head 108, the needle catch 124, the needle exit port 126, the opening 128, the needle carrier 130, a wire form 600, a center tube 602, a spring 604, a first washer member 606, a second washer member 608, a pusher wire 610, and a securing member 612. The actuator 102 includes a button 614, a shaft 616, and a bearing 618. The bearing 618 is configured for receiving the wire form 600. The wire form 600 is inserted into the bearing 618, thereby coupling it to the actuator 102. The wire form 600 is housed within the center tube 602 within the handle 104. The wire form 600 extends through the elongated shaft member 106 to prevent kinking of the elongated shaft member 106. The spring 604 encircles the wire form 600, and the center tube 602 and the spring 604 is compressed between the actuator 102 and the first washer member 606. The handle 104 encases the actuator 102, the wire form 600, the center tube 602, the spring 604, the first washer member 606, and a portion of the elongated shaft member 106. In another embodiment, the medical device 100 may be constructed without the spring 604, thereby requiring the operator to manually manipulate the actuator 102. The handle 104 may be constructed to accommodate various ergonomic designs.

Figure 6B:
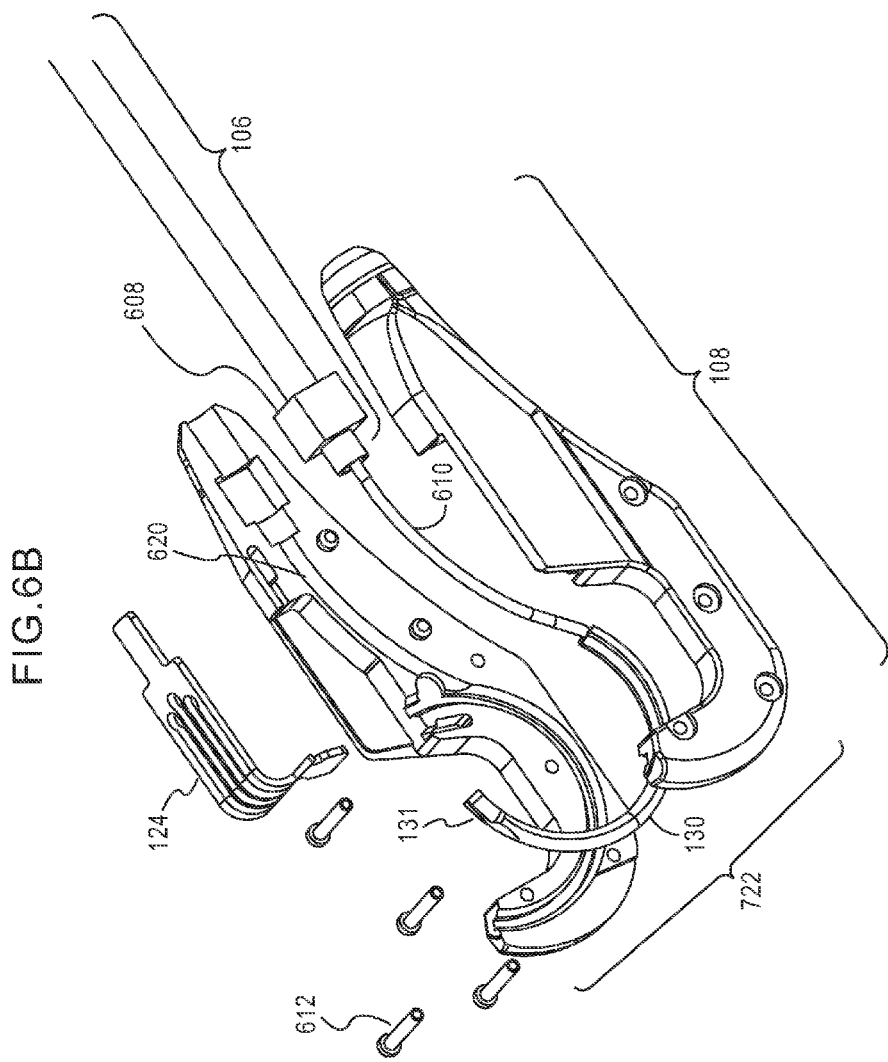
FIG. 6B is an exploded broken view of the head of FIG. 6A.

Referring to FIGS. 6A and 6B, the elongated shaft member 106 extends from and through the first washer member 606, and through the second washer member 608. In one embodiment, each of the first washer member 606 and the second washer member 608 is substantially cube-shaped. In other embodiments, each of the first washer member 606 and the second washer member 608 is substantially cylindrical-shaped or key-shaped. The key-shape may be used to prevent rotation of the head 108. The cylindrical shape of the second washer member 608 facilitates the rotation of the head 108. The pusher wire 610 extends from the second washer member 608. The pusher wire 610 is attached to the wire form 600. The pusher wire 610 may be attached to the wire form 600 by, for example, a weld, a crimp, a coupling, an adhesive, or other means. Each of the elongated shaft member 106 and the pusher wire 610 may be constructed from a shape memory material, such as Nitinol™. Other metals that may be used include, but are not limited to, nickel, copper, stainless steel, cobalt, vanadium, chromium, iron, and super-elastic metallic alloys. The shape memory material used to construct the elongated shaft member 106 and the pusher wire 610 allow for bendability and high column strength when constrained. The elongated shaft member 106 is deflectable off of the longitudinal axis, such that the elongated shaft member 106 is able to transmit torque to manipulate the head 108. In another embodiment, the elongated shaft member 106 is a coil to allow greater flexibility. The coil may be covered by, for example, a flexible sleeve.

The pusher wire 610 extends to the needle carrier 130, which is encased by the head 108. The head 108 is comprised of two parallel or substantially parallel flat outer surfaces. The head 108 includes a channel 620 to prevent binding of the pusher wire 610, and facilitate a smooth transition between the pusher wire 610 and the needle carrier 130. The securing member 612, such as a rivet, is used to couple the two substantially parallel heads 108.

In various embodiments, other means may be used to construct the medical device 100, including, but not limited to, glue, welding, sonic welding, insert molding, or use of fasteners. The elongated shaft member 106 can be of a shape other than tubular or cylindrical, such as elliptical or rectangular. The shape and material chosen for the medical device 100 will vary to suit a particular application.

Referring to FIG. 7A, in one embodiment according to the invention, the medical device 100 may have the following dimensions. These dimensions are merely exemplary and other dimensions may be contemplated. For example, a length 700 of the actuator 102 is about 3 inches. A width 701 of the actuator 102 is about 0.86 inches. A length 702 of the handle 104 is about 5.5 inches. A length 703 of the proximal end 110 of the handle 104 is about 2 inches. A diameter 704 of the handle 104 is about 0.345 inches. A length 708 of the elongated shaft member 106 from the proximal end 114 to the distal end 116 (FIG. 1A) is about 5.25 inches.

Referring to FIG. 7B, an inner diameter 710 of the elongated shaft member 106 is about 0.06 inches. An outer diameter 712 of the elongated shaft member 106 is about 0.08 inches. A length 714 of the head 108 is about 1.5 inches. A width 716 of the head 108 is about 0.46 inches, a width 718 of the opening 128 is about 0.29 inches, and a length 720 of the opening 128 is about 0.4 inches. Referring now to FIG. 6B, a thickness 722 of the head 108 is about 0.20 inches when the two portions are coupled together.

Referring to FIGS. 6B, 7A, and 7B, the length 714 of the head 108 is measured along the longitudinal axis of the medical device 100. The maximum width 716 of the head 108 is measured in a first direction that is transverse to the longitudinal axis of the medical device 100, and the thickness 722 of the head 108 is measured in a second direction that is perpendicular to the first direction. The length 714 of the head 108 is greater than the maximum width 716 of the head 108. The maximum width 716 of the head 108 is greater than the thickness 722 of the head 108, and the thickness 722 of the head 108 is greater than the outer diameter 712 of the elongated shaft member 106.

It will be understood that various modifications may be made to the embodiments disclosed herein. Therefore, the above description should not be construed as limiting, but merely as illustrative of some embodiments according to the invention.

What is claimed is:

1. A medical device for use in a transvaginal implant procedure, comprising:
a handle having a proximal end and a distal end, the handle including an actuator configured to be manipulated by an operator of the medical device, the handle including a first washer member;
an elongated shaft member having a diameter and a length, the elongated shaft member defining a lumen and extending from the distal end of the handle, the diameter being minimally greater than a diameter of a wire form extending longitudinally within the elongated shaft member, the elongated shaft member extending along a longitudinal axis when the elongated shaft member is disposed in a straight or a substantially straight configuration; and
a head extending over a distal end of the elongated shaft member, the head including a second washer member, the head having a length measured along the longitudinal axis, a maximum width measured in a first direction transverse to the longitudinal axis, and a thickness measured in a second direction perpendicular to the first direction, the length of the head being greater than the maximum width and the maximum width being greater than the thickness, the thickness being greater than the diameter of the elongated shaft member, the head including a needle carrier configured to receive a needle that can be coupled to a suture or to a portion of a pelvic floor repair implant, the head further including a needle catch and a needle exit port, at least a portion of the needle carrier exiting the needle exit port when the operator manipulates the actuator, the needle catch configured to receive and retain the needle carried by the needle carrier,
the elongated shaft member being composed of a flexible material that extends the length of the elongated shaft member from the handle to the head such that the elongated shaft member can bend in a plurality of directions off the longitudinal axis of the elongated shaft member, the elongated shaft member extending between and through the first washer member and the second washer member.

2. The medical device of claim 1 wherein the handle includes a tubular shaft having a tapered distal portion, the handle including a spring that is entirely disposed between the tapered distal portion of the tubular shaft of the handle and the proximal end of the handle, the actuator being configured to cause compression of the spring when the actuator is manipulated by the operator of the medical device.

3. The medical device of claim 1 wherein the handle also includes a handle portion configured to be grasped by the operator of the medical device and a tubular shaft, the tubular shaft having a tapered distal tip.

4. The medical device of claim 1 wherein the wire form moves longitudinally within the elongated shaft member which causes the needle carrier to exit the needle exit port when the operator depresses the actuator.

5. The medical device of claim 1 wherein the elongated shaft member has an outer surface that is exposed such that the operator can touch the outer surface while manipulating the actuator during the transvaginal implant procedure and is deflectable off the longitudinal axis by manipulation by the operator.

6. The medical device of claim 1 wherein the elongated shaft member is bendable into a bent shape at a plurality of locations along the length of the elongated shaft member, the bent shape being substantially retained during use of the medical device.

7. The medical device of claim 1 wherein the head includes a channel in which the needle carrier is disposed and the needle carrier is movable within the channel by the operator manipulating the actuator.

8. The medical device of claim 1 wherein the head defines an opening for receiving tissue of a patient's body and is rotatable around the longitudinal axis of the elongated shaft member.

9. The medical device of claim 8 wherein the opening includes a substantially C-shaped configuration.

10. The medical device of claim 1 wherein each of the first washer member and the second washer member has a shape configured to prevent rotation of the head.

11. The medical device of claim 1 wherein the elongated shaft member includes a shape memory material, the elongated shaft member is configured to bend from an original shape into a bent shape at a plurality of locations along the length of the elongated shaft member when pressure is applied to the elongated shaft member, the elongated shaft member is configured to revert back to the original shape when the pressure is removed.

12. The medical device of claim 1 further comprising an elongated lumen member for transporting a sling.

13. The medical device of claim 1 wherein a proximal end of the wire form is operatively coupled to the actuator and a distal end of the wire form is operatively coupled to the needle carrier such that the wire form extends through the elongated shaft member, the wire form and the elongated shaft member being constructed of a shape memory material.

14. The medical device of claim 1 wherein the handle includes a spring that is entirely disposed between the first washer member and the proximal end of the handle.

15. The medical device of claim 1 wherein the actuator comprises a trigger.

16. A medical device for use in a transvaginal implant procedure, comprising:
   a handle including a spool member and a ring member, the spool member configured for receiving at least two fingers of an operator of the medical device, the ring member configured for receiving a thumb of the operator, the handle including a first washer member;
   an elongated shaft member having a diameter and a length, the elongated shaft member defining a lumen and extending from a distal end of the handle, the diameter being minimally greater than a diameter of a wire form extending longitudinally within the elongated shaft member, the elongated shaft member extending along a longitudinal axis when the elongated shaft member is disposed in a straight or a substantially straight configuration; and
   a head extending over a distal end of the elongated shaft member, the head including a second washer member, the head having a length measured along the longitudinal axis, a maximum width measured in a first direction transverse to the longitudinal axis, and a thickness measured in a second direction perpendicular to the first direction, the length of the head being greater than the maximum width and the maximum width being greater than the thickness, the thickness being greater than the diameter of the elongated shaft member, the head including a needle carrier configured to receive a needle that can be coupled to a suture or to a portion of a pelvic floor repair implant, the head further including a needle catch and a needle exit port, at least a portion of the needle carrier exiting the needle exit port when the operator manipulates the handle, the needle catch configured to receive and retain the needle carried by the needle carrier,
   the elongated shaft member being composed of a flexible material that extends the length of the elongated shaft member from the handle to the head such that the elongated shaft member can bend in a plurality of directions off the longitudinal axis of the elongated shaft member, the elongated shaft member extending between and through the first washer member and the second washer member.

17. The medical device of claim 16 wherein the wire form moves longitudinally within the elongated shaft member which causes the needle carrier to exit the needle exit port when the operator manipulates the handle.

18. The medical device of claim 16 wherein the elongated shaft member has an outer surface that is exposed such that the operator can touch the outer surface while manipulating the handle during the transvaginal implant procedure and is deflectable off the longitudinal axis by manipulation by the operator.

19. The medical device of claim 16 wherein the head includes a channel in which the needle carrier is disposed and the needle carrier is movable within the channel by the operator manipulating the handle.

20. A method of delivering a pelvic floor repair implant, the method comprising:
   providing a medical device, the medical device includes a handle having a proximal end and a distal end, the handle including an actuator configured to be manipulated by an operator of the medical device, the handle including a first washer member, an elongated shaft member having a diameter, the elongated shaft member defining a lumen and extending from the distal end of the handle, the diameter being minimally greater than a diameter of a wire form extending longitudinally within the elongated shaft member, the elongated shaft member extending along a longitudinal axis when the elongated shaft member is disposed in a straight or a substantially straight configuration, a head extending over a distal end of the elongated shaft member, the head having a length measured along the longitudinal axis, a maximum width measured in a first direction transverse to the longitudinal axis, and a thickness measured in a second direction perpendicular to the first direction, the length being greater than the maximum width and the maximum width being greater than the thickness, the thickness being greater than the diameter of the elongated shaft member, the head including a second washer member, the head including a needle carrier configured to receive a needle that can be coupled to a portion of a pelvic floor repair implant, the head further including a needle catch and a needle exit port, at least a portion of the needle carrier exiting the needle exit port when the operator manipulates the actuator, the needle catch configured to receive and retain the needle carried by the needle carrier, the elongated shaft member being composed of a flexible material that extends a length of the elongated shaft member from the handle to the head such that the elongated shaft member can bend in a plurality of directions off the longitudinal axis of the elongated shaft member, the elongated shaft member extending between and through the first washer member and the second washer member;
   inserting the needle coupled to the portion of the pelvic floor repair implant into the needle carrier;

dissecting a patient's body to create an opening to a pelvic region of the patient's body;
inserting the elongated shaft member and the head through the opening of the pelvic region;
manipulating the head and an opening of the head onto a ligament within the pelvic region; and
deploying the needle carrier out of the needle exit port and pushing the needle and the pelvic floor repair implant through the ligament.

* * * * *